US011890142B2

(12) United States Patent
Tsymbalenko

(10) Patent No.: US 11,890,142 B2
(45) Date of Patent: Feb. 6, 2024

(54) SYSTEM AND METHODS FOR AUTOMATIC LESION CHARACTERIZATION

(71) Applicant: GE Precision Healthcare LLC, Milwaukee, WI (US)

(72) Inventor: Yelena Viktorovna Tsymbalenko, Mequon, WI (US)

(73) Assignee: GE PRECISION HEALTHCARE LLC, Milwaukee, WI (US)

(*) Notice: Subject to any disclaimer, the term of this patent is extended or adjusted under 35 U.S.C. 154(b) by 435 days.

(21) Appl. No.: 16/741,373

(22) Filed: Jan. 13, 2020

(65) Prior Publication Data

US 2021/0212665 A1 Jul. 15, 2021

(51) Int. Cl.
| | | |
|---|---|---|
| A61B 8/00 | (2006.01) | |
| A61B 8/08 | (2006.01) | |
| G06T 7/10 | (2017.01) | |
| A61B 8/14 | (2006.01) | |
| G06N 3/08 | (2023.01) | |
| G06N 3/04 | (2023.01) | |

(52) U.S. Cl.
CPC .............. *A61B 8/469* (2013.01); *A61B 8/463* (2013.01); *A61B 8/485* (2013.01); *A61B 8/5223* (2013.01); *A61B 8/5246* (2013.01); *G06N 3/08* (2013.01); *G06T 7/10* (2017.01); *A61B 8/14* (2013.01); *G06N 3/04* (2013.01); *G06T 2207/10132* (2013.01); *G06T 2207/20081* (2013.01); *G06T 2207/30096* (2013.01)

(58) Field of Classification Search
CPC ......... A61B 8/469; A61B 8/463; A61B 8/485; A61B 8/5223; A61B 8/5246; G06T 7/10; G06T 2207/10132; G06T 2207/30096
See application file for complete search history.

(56) References Cited

U.S. PATENT DOCUMENTS

| | | | |
|---|---|---|---|
| 8,298,147 B2 | 10/2012 | Huennekens et al. | |
| 2006/0036167 A1 | 2/2006 | Shina | |
| 2006/0058666 A1* | 3/2006 | Tanigawa | ............ G01S 7/52053 600/441 |
| 2009/0203986 A1* | 8/2009 | Winnick | ................ G16H 40/63 600/407 |
| 2015/0265252 A1* | 9/2015 | Chu | ...................... A61B 8/5269 600/431 |
| 2016/0192840 A1* | 7/2016 | Chang | .................. A61B 5/0095 600/407 |
| 2020/0046324 A1* | 2/2020 | Veronesi | ................... G06T 7/40 |

OTHER PUBLICATIONS

Menezes et al., "Correlation of Strain Elastography with Conventional Sonography and FNAC/Biopsy", 2016, Journal of Clinical and Diagnostic Research, vol. 10(7), 5-10 (Year: 2016).*

(Continued)

*Primary Examiner* — Colin T. Sakamoto
*Assistant Examiner* — Andrew W Begeman
(74) *Attorney, Agent, or Firm* — McCoy Russell LLP

(57) ABSTRACT

Methods and systems are provided for automatically characterizing lesions in ultrasound images. In one example, a method includes automatically determining an A/B ratio of a region of interest (ROI) via an A/B ratio model that is trained to output the A/B ratio using a B-mode image of the ROI and an elastography image of the ROI as inputs, and displaying the A/B ratio on a display device.

19 Claims, 4 Drawing Sheets

(56) References Cited

OTHER PUBLICATIONS

Zhang et al., "Dual-mode artificially-intelligent diagnosis of breast tumours in shear-wave elastography and B-mode ultrasound using deep polynomial networks", 2019, Medical Engineering Physics, 64, 1-6 (Year: 2019).*
Dietrich et al., "Strain Elastography—How To Do It?", 2017, Ultrasound Int Open, 3, 137-149 (Year: 2017).*
Wierman, "Understanding Gain in Ultrasound", Feb. 5, 2019, E.I. Medical Imaging (Year: 2019).*
Dietrich et al., "EUS elastography: How to do it?", Feb. 15, 2018, Endoscopic Ultrasound, vol. 7, Issue 1, p. 20-28 (Year: 2018).*
Ge, "Shear Wave Elastography: Abdominal Imaging", 2014, DOC1584626 (Year: 2014).*
Barr, R., "Future of breast elastography," Ultrasonography, vol. 38, No. 2, Apr. 2019, 13 pages.

* cited by examiner

SYSTEM AND METHODS FOR AUTOMATIC LESION CHARACTERIZATION

TECHNICAL FIELD

Embodiments of the subject matter disclosed herein relate to ultrasound imaging, and more particularly, to characterizing lesions imaged with ultrasound imaging.

BACKGROUND

Medical ultrasound is an imaging modality that employs ultrasound waves to probe the internal structures of a body of a patient and produce a corresponding image. For example, an ultrasound probe comprising a plurality of transducer elements emits ultrasonic pulses which reflect or echo, refract, or are absorbed by structures in the body. The ultrasound probe then receives reflected echoes, which are processed into an image. Ultrasound images of the internal structures may be saved for later analysis by a clinician to aid in diagnosis and/or displayed on a display device in real time or near real time.

SUMMARY

In one embodiment, a method includes automatically determining an A/B ratio of a region of interest (ROI) via an A/B ratio model that is trained to output the A/B ratio using a B-mode image of the ROI and an elastography image of the ROI as inputs, and displaying the A/B ratio on a display device.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

DETAILED DESCRIPTION

Ultrasound images acquired during a medical ultrasound exam may be used to diagnose a patient condition, which may include one or more clinicians analyzing the ultrasound images for abnormalities, measuring certain anatomical features imaged in the ultrasound images, and so forth. For example, when characterizing a lesion, such as a breast lesion, a clinician may evaluate the lesion using standard B-mode ultrasound imaging as well as elastography imaging, which is a mechanism for non-invasively measuring tissue stiffness. Certain properties of the lesion in the elastography image relative to the lesion in the B-mode image may facilitate semi-quantitative characterization of the lesion. For example, the width and/or area of the lesion in the elastography image relative to the width and/or area of the lesion in the B-mode image, which is referred to as an A/B ratio, may provide a semi-quantitative analysis of the malignancy of the lesion, as benign lesions typically have a smaller A/B ratio than malignant lesions.

Thus, when characterizing a lesion such as a breast lesion, a clinician may measure the A/B ratio by acquiring a B-mode image that includes a lesion and acquiring a corresponding elastography image including the lesion. The clinician may then identify the lesion in each image, measure the width of the lesion in each image, and then calculate the A/B ratio. However, this process is time-consuming and may lead to inconsistent A/B ratio calculations across different clinicians and different patients, and even across different imaging sessions of the same patient. In particular, if the A/B ratio is monitored for a patient over time to track lesion development, inconsistent A/B ratio calculations may lead to inaccurate determinations of lesion growth and/or transformation, which could negatively impact patient care.

Thus, according to embodiments disclosed herein, an A/B ratio of a target anatomical feature, such as a lesion, may be calculated automatically using an artificial intelligence-based model that is trained to segment the target anatomical feature in both a B-mode image and an elastography image, measure a width and/or area of the segmented target anatomical feature in each image, and calculate the A/B ratio from the measured widths and/or areas. The automatically calculated A/B ratio may be displayed on a display device and/or saved as part of a patient exam (e.g., in the patient's medical record). In doing so, A/B ratio measurement may be more consistent across different patients and across different imaging sessions, which may improve patient care and reduce clinician workflow demands.

Figure 1:
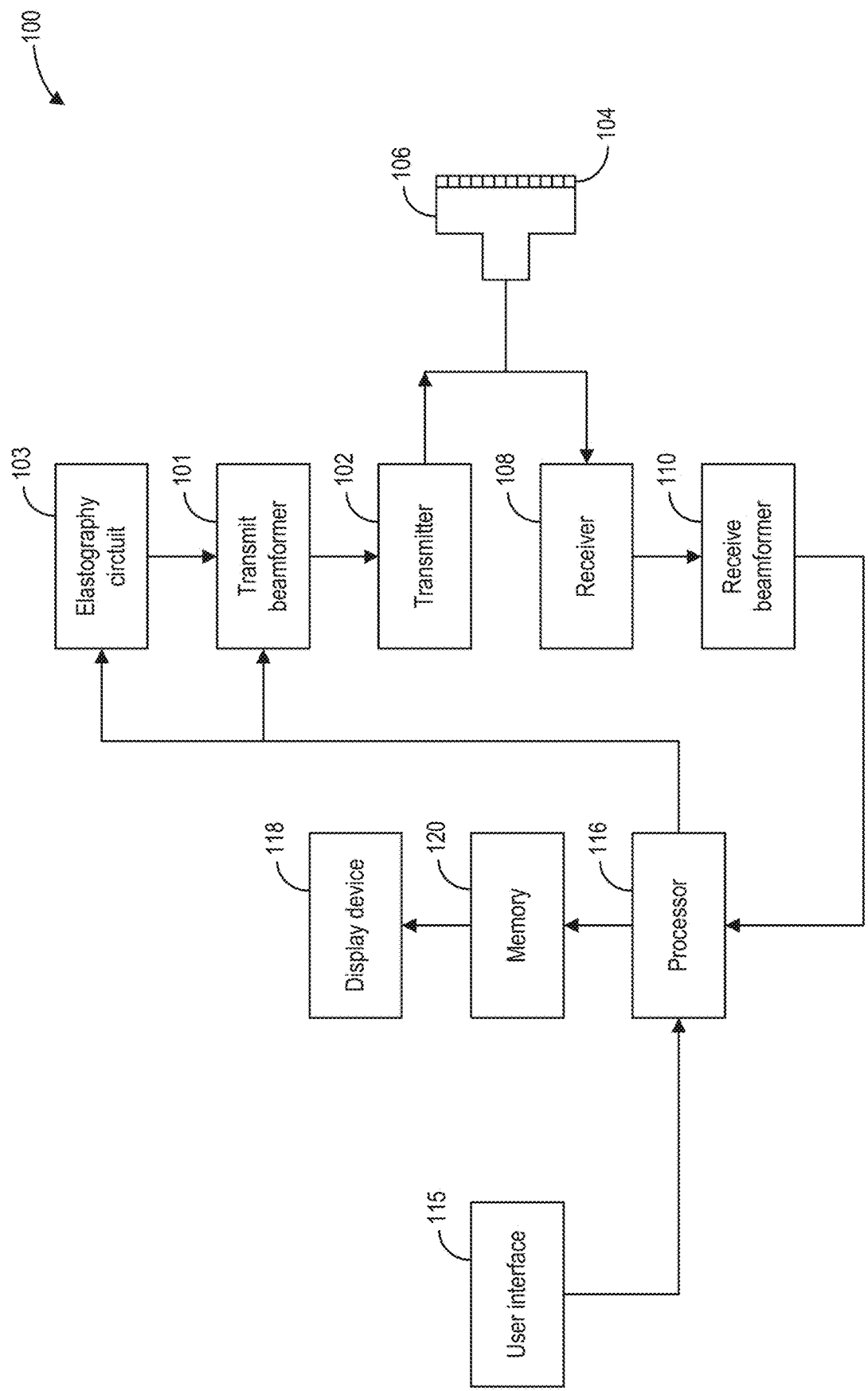
FIG. 1 shows a block diagram of an ultrasound system, according to an embodiment.
Figure 2:
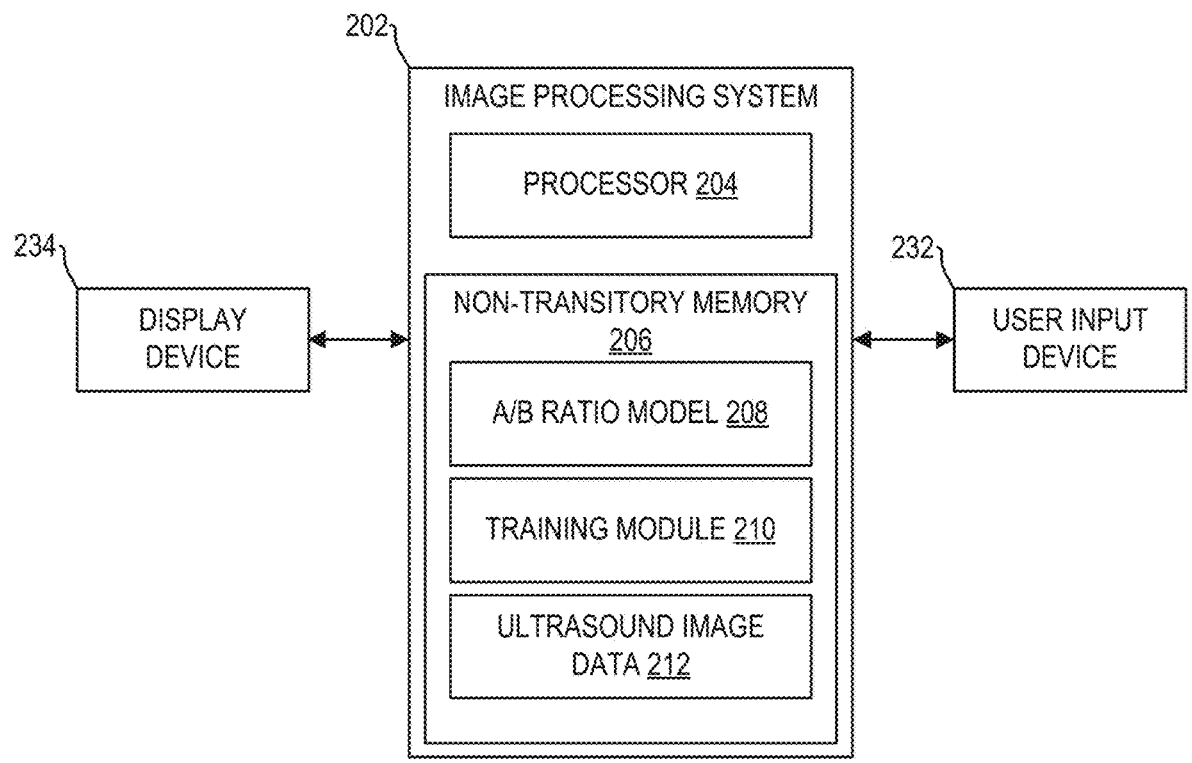
FIG. 2 is a schematic diagram illustrating a system for automatic lesion characterization, according to an embodiment.

An ultrasound imaging system, such as the ultrasound imaging system of FIG. 1, may be used to obtain B-mode images and elastography images, which may be entered as input to an A/B ratio model stored on an image processing system, such as the image processing system of FIG. 2. The A/B ratio model may be trained to segment a lesion in a B-mode image and a corresponding elastography image and calculate the A/B ratio, according to the method shown in FIG. 3. The calculated A/B ratio may be output for display on a display device, such as part of the graphical user interface shown in FIG. 4.

Referring to FIG. 1, a schematic diagram of an ultrasound imaging system 100 in accordance with an embodiment of the disclosure is shown. The ultrasound imaging system 100 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body (not shown). According to an embodiment, the probe 106 may be a one-dimensional transducer array probe. However, in some embodiments, the probe 106 may be a two-dimensional matrix transducer array probe. As explained further below, the transducer elements 104 may be comprised of a piezoelectric material. When a voltage is applied to a piezoelectric crystal, the crystal physically expands and contracts, emitting an ultrasonic spherical wave. In this way, transducer elements 104 may convert electronic transmit signals into acoustic transmit beams.

After the elements 104 of the probe 106 emit pulsed ultrasonic signals into a body (of a patient), the pulsed ultrasonic signals are back-scattered from structures within an interior of the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs radio frequency (RF) data. Additionally, transducer element 104 may produce one or more ultrasonic pulses to form one or more transmit beams in accordance with the received echoes.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. In one embodiment, data acquired via ultrasound system 100 may be used to train a machine learning model. A user interface 115 may be used to control operation of the ultrasound imaging system 100, including to control the input of patient data (e.g., patient medical history), to change a scanning or display parameter, to initiate a probe repolarization sequence, and the like. The user interface 115 may include one or more of the following: a rotary element, a mouse, a keyboard, a trackball, hard keys linked to specific actions, soft keys that may be configured to control different functions, and a graphical user interface displayed on a display device 118.

The ultrasound imaging system 100 also includes a processor 116 to control the transmit beamformer 101, the transmitter 102, the receiver 108, and the receive beamformer 110. The processer 116 is in electronic communication (e.g., communicatively connected) with the probe 106. For purposes of this disclosure, the term "electronic communication" may be defined to include both wired and wireless communications. The processor 116 may control the probe 106 to acquire data according to instructions stored on a memory of the processor, and/or memory 120. The processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates IQ data pairs representative of the echo signals. In another embodiment, the demodulation can be carried out earlier in the processing chain. The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire images at a real-time rate of 7-20 frames/sec. The ultrasound imaging system 100 may acquire 2D data of one or more planes at a significantly faster rate. However, it should be understood that the real-time frame-rate may be dependent on the length of time that it takes to acquire each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data, for example by augmenting the data, prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on display device 118. Other embodiments may acquire and display data at different rates. For example, some embodiments may acquire data at a frame-rate of less than 10 Hz or greater than 30 Hz depending on the size of the frame and the intended application. A memory 120 is included for storing processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present invention, data may be processed in different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by display device 118.

The ultrasound imaging system 100 includes an elastography circuit 103 configured to enable shear-wave and/or stain elastography imaging. While in the shear-wave mode, the elastography circuit 103 may control the probe 106 to generate a shear wave at a site within a region of interest (ROI) of an imaging subject (e.g., a patient). The elastography circuit 103 may control the probe 106 or, more particularly, the transducer elements 104 to direct a shear-wave generating or pushing pulse(s) toward the predetermined site to generate the shear-wave. Alternatively, the elastography circuit 103 may control another device capable of generating shear-waves and the probe 106 may measure or track the velocity as the shear-wave passes through the ROI. For example, the elastography circuit 103 may control a therapy transducer, a mechanical actuator, or an audio device to generate the shear waves.

While in the strain mode, the elastography circuit 103 may control the probe 106 to generate a mechanical force (e.g., surface vibration, freehand or step quasi-static surface displacement, or the like) or radiation force on the patient or ROI to measure the stiffness or strain of the ROI of the patient. Alternatively, the elastography circuit 103 may control another device capable of generating a mechanical force on the patient or the ROI. For example, a low frequency mechanical vibrator may be applied to the skin surface and the compression motion induced in the underlying tissue, such as on the ROI, is measured by the probe 106.

In various embodiments of the present disclosure, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

After performing a two-dimensional ultrasound scan, a block of data comprising scan lines and their samples is generated. After back-end filters are applied, a process known as scan conversion is performed to transform the two-dimensional data block into a displayable bitmap image with additional scan information such as depths, angles of each scan line, and so on. During scan conversion, an interpolation technique is applied to fill missing holes (i.e., pixels) in the resulting image. These missing pixels occur because each element of the two-dimensional block should typically cover many pixels in the resulting image. For example, in current ultrasound imaging systems, a bicubic interpolation is applied which leverages neighboring elements of the two-dimensional block. As a result, if the two-dimensional block is relatively small in comparison to the size of the bitmap image, the scan-converted image will include areas of poor or low resolution, especially for areas of greater depth.

Ultrasound images acquired by ultrasound imaging system 100 may be further processed. In some embodiments, ultrasound images produced by ultrasound imaging system 100 may be transmitted to an image processing system, where in some embodiments, the ultrasound images may be segmented by a machine learning model trained using ultrasound images and corresponding ground truth output. As used herein, ground truth output refers to an expected or "correct" output based on a given input into a machine learning model. For example, if a machine learning model is being trained to classify images of cats, the ground truth output for the model, when fed an image of a cat, is the label "cat". In addition, the image processing system may further process the ultrasound images with one or more different machine learning models configured to calculate an AB ratio based on the segmented ultrasound images.

Although described herein as separate systems, it will be appreciated that in some embodiments, ultrasound imaging system 100 includes an image processing system. In other embodiments, ultrasound imaging system 100 and the image processing system may comprise separate devices. In some embodiments, images produced by ultrasound imaging system 100 may be used as a training data set for training one or more machine learning models, wherein the machine learning models may be used to perform one or more steps of ultrasound image processing, as described below.

Referring to FIG. 2, image processing system 202 is shown, in accordance with an embodiment. In some embodiments, image processing system 202 is incorporated into the ultrasound imaging system 100. For example, the image processing system 202 may be provided in the ultrasound imaging system 100 as the processor 116 and memory 120. In some embodiments, at least a portion of image processing 202 is disposed at a device (e.g., edge device, server, etc.) communicably coupled to the ultrasound imaging system via wired and/or wireless connections. In some embodiments, at least a portion of image processing system 202 is disposed at a separate device (e.g., a workstation) which can receive images from the ultrasound imaging system or from a storage device which stores the images/data generated by the ultrasound imaging system. Image processing system 202 may be operably/communicatively coupled to a user input device 232 and a display device 234. The user input device 232 may comprise the user interface 115 of the ultrasound imaging system 100, while the display device 234 may comprise the display device 118 of the ultrasound imaging system 100, at least in some examples.

Image processing system 202 includes a processor 204 configured to execute machine readable instructions stored in non-transitory memory 206. Processor 204 may be single core or multi-core, and the programs executed thereon may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration.

Non-transitory memory 206 may store an A/B ratio model 208, training module 210, and ultrasound image data 212. A/B ratio model 208 may include one or more machine learning models, such as deep learning networks, comprising a plurality of weights and biases, activation functions, loss functions, gradient descent algorithms, and instructions for implementing the one or more deep neural networks to process input ultrasound images. For example, A/B ratio model 208 may store instructions for implementing a segmentation model trained to identify and segment a target anatomical feature, such as a lesion, in both B-mode images and elastography images. A/B ratio model 208 may store further instructions for calculating an A/B ratio from segmented B-mode and elastography images. The A/B ratio model 208 may include one or more neural networks. The A/B ratio model 208 may include trained and/or untrained neural networks and may further include training routines, or parameters (e.g., weights and biases), associated with one or more neural network models stored therein.

Thus, the A/B ratio model 208 described herein may be deployed to automatically calculate an A/B ratio of an anatomical feature such as a lesion. In some examples, the A/B ratio model 208 may use a U-net or other convolutional neural network architecture to segment a lesion in corresponding B-mode and elastography images (e.g., images taken of the same ROI, and in some examples at approximately the same time) and may be trained using B-mode and elastography ultrasound images and/or cine loops where lesions have been annotated/identified by experts. The A/B ratio model 208 may measure a width of the segmented lesion in both the B-mode image and the elastography image (e.g., the A/B ratio model 208 may identify the widest part of the lesion and measure the widest part of the lesion to determine the width of the lesion). The A/B ratio may be calculated as the ratio of the width of the lesion in the elastography image to the width of the lesion in the B-mode image. In other examples, the area of each lesion may be determined from the measured widths or another suitable determination and the A/B ratio may be calculated as the area of the lesion in the elastography image to the area of the lesion in the B-mode image.

Non-transitory memory 206 may further include training module 210, which comprises instructions for training one or more of the machine learning models stored in the A/B ratio model 208. In some embodiments, the training module 210 is not disposed at the image processing system 202. The A/B ratio model 208 thus includes trained and validated network(s).

Non-transitory memory 206 may further store ultrasound image data 212, such as ultrasound images captured by the ultrasound imaging system 100 of FIG. 1. The ultrasound image data 212 may include both B-mode images and elastography images (whether obtained using shear-wave elastography or strain elastography). Further, ultrasound image data 212 may store ultrasound images, ground truth output, iterations of machine learning model output, and other types of ultrasound image data that may be used to train the A/B ratio model 208, when training module 210 is stored in non-transitory memory 206. In some embodiments, ultrasound image data 212 may store ultrasound images and ground truth output in an ordered format, such that each ultrasound image is associated with one or more corresponding ground truth outputs. For example, ultrasound image data 212 may store sets of training data, where each set includes a B-mode image and a ground truth that includes a region of interest (ROI) annotated by an expert (e.g., a lesion annotated by a clinician) and/or an elastography image and a ground truth including an ROI annotated by an expert (e.g., a lesion annotated by a clinician). In some examples, one or more sets of training data may include a B-mode image and an elastography image acquired on the same patient (e.g., such that the same lesion is annotated on both images). In some examples, one or more sets of training data may include B-mode and/or elastography images that do not include lesions, and thus do not include expert annotations. Further, in examples where training module 210 is not disposed at the image processing system 202, the images/ground truth output usable for training the A/B ratio model 208 may be stored elsewhere.

In some embodiments, the non-transitory memory 206 may include components disposed at two or more devices, which may be remotely located and/or configured for coordinated processing. In some embodiments, one or more aspects of the non-transitory memory 206 may include remotely-accessible networked storage devices configured in a cloud computing configuration.

User input device 232 may comprise one or more of a touchscreen, a keyboard, a mouse, a trackpad, a motion sensing camera, or other device configured to enable a user to interact with and manipulate data within image processing system 202. In one example, user input device 232 may enable a user to make a selection of an ultrasound image to use in training a machine learning model, to indicate or label a position of an ROI in the ultrasound image data 212, or for further processing using a trained machine learning model.

Display device 234 may include one or more display devices utilizing virtually any type of technology. In some embodiments, display device 234 may comprise a computer monitor, and may display ultrasound images. Display device 234 may be combined with processor 204, non-transitory memory 206, and/or user input device 232 in a shared enclosure, or may be peripheral display devices and may comprise a monitor, touchscreen, projector, or other display device known in the art, which may enable a user to view ultrasound images produced by an ultrasound imaging system, and/or interact with various data stored in non-transitory memory 206.

It should be understood that image processing system 202 shown in FIG. 2 is for illustration, not for limitation. Another appropriate image processing system may include more, fewer, or different components.

Figure 3:
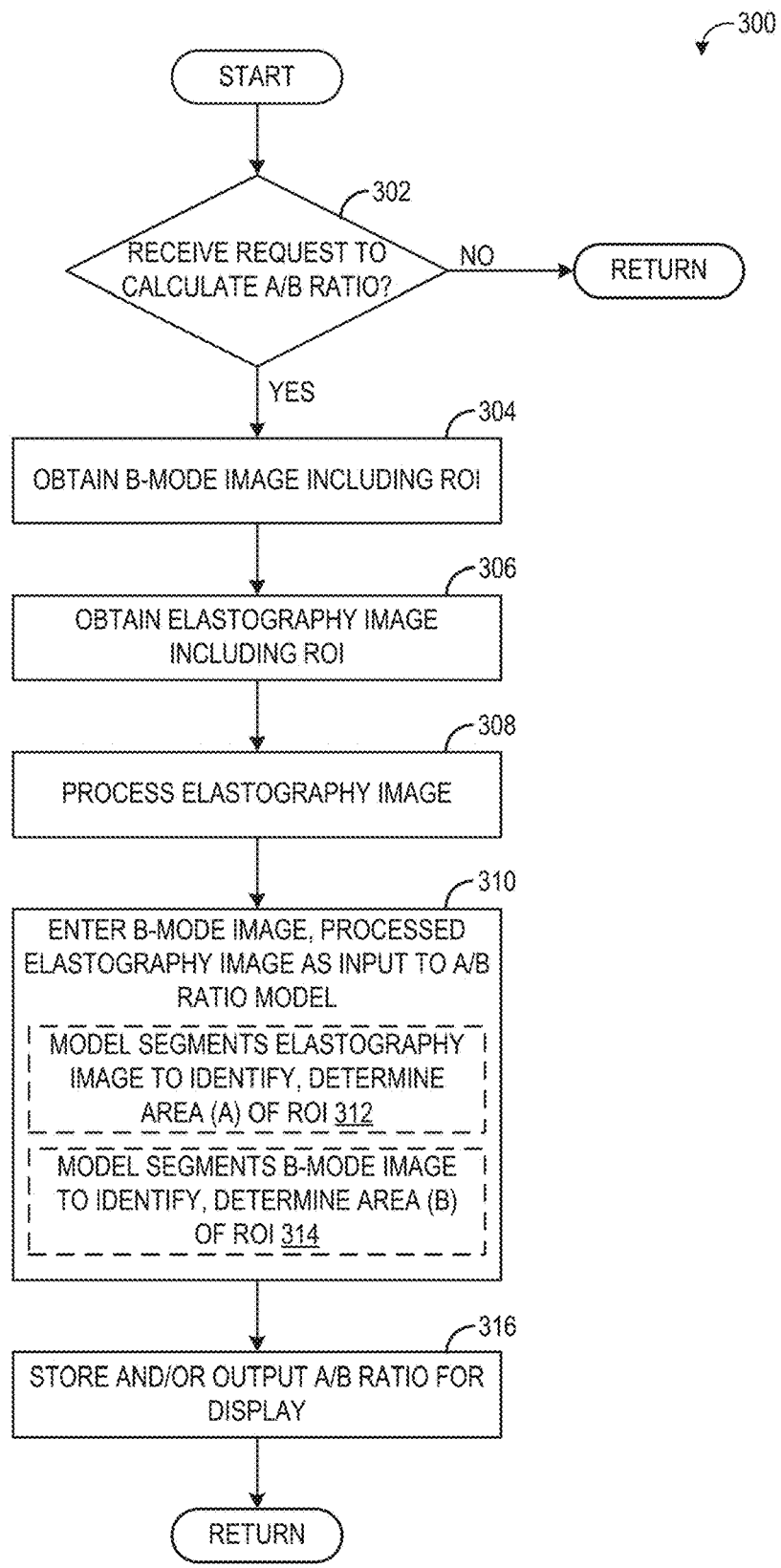
FIG. 3 is a flow chart illustrating a method for automatically calculating an A/B ratio, according to an embodiment.

FIG. 3 shows a flow chart illustrating an example method 300 for automatically calculating an A/B ratio on an ROI, such as a breast lesion, according to an embodiment. Method 300 is described with regard to the systems and components of FIGS. 1-2, though it should be appreciated that the method 300 may be implemented with other systems and components without departing from the scope of the present disclosure. Method 300 may be carried out according to instructions stored in non-transitory memory of a computing device, such as image processing system 202 of FIG. 2.

At 302, method 300 includes determining if a request to calculate an A/B ratio has been received. The request to calculate the A/B ratio may be received via user input. For example, an operator of the ultrasound imaging system may enter an input via a user input device (e.g., user interface 115 and/or user input device 232) requesting that an A/B ratio be calculated. In some examples, the user input requesting the A/B ratio be calculated may be received while the operator is actively imaging a patient, and thus the request may include a request to calculate an A/B ratio using a particular image or series of images (e.g., a most currently acquired or stored elastography image). In some examples, the request to calculate the A/B ratio may include an indication of whether the A/B ratio is to be calculated from the widths of a region of interest (e.g., lesion) in the elastography and B-mode images or whether the A/B ratio is to be calculated from the areas of the region of interest in the elastography and B-mode images. In some examples, the request to calculate the A/B ratio may be received from the ultrasound imaging system as part of an automated or semi-automated workflow.

If a request to calculate an A/B ratio has not been received, method 300 returns. When no request is received to calculate an A/B ratio, the ultrasound system may continue to acquire ultrasound images (whether in B-mode, elastography mode, or other imaging mode) when requested (e.g., when the ultrasound probe is powered on and in contact with an imaging subject), and may continue to assess if a request to calculate an A/B ratio is received.

If a request to calculate an A/B ratio is received, method 300 proceeds to 304 to obtain a B-mode image that includes a region of interest (ROI). The ROI may be a lesion or another anatomical feature of interest, such as a thyroid. In some examples, the request to calculate the A/B ratio may include an indication of which anatomical feature/ROI the A/B ratio is to be calculated (e.g., a request to calculate an A/B ratio on a breast lesion). The B-mode image that is obtained at 304 may include the indicated anatomical feature/ROI. The B-mode image may be a standard, 2D grayscale image obtained via an ultrasound probe (e.g., probe 106) while the probe is operated under B-mode imaging. The B-mode image that is obtained at 304 may be acquired by the ultrasound system in response to the request to calculate the A/B ratio. In other examples, the B-mode image may be obtained from memory. In some examples, the B-mode image obtained at 304 may be selected by a user, e.g., the operator of the ultrasound imaging system may select a B-mode image from a plurality of B-mode images stored in memory of the ultrasound imaging system, or the operator may indicate via user input that a currently-displayed B-mode image may be used for the A/B ratio calculation. In some examples, the B-mode image obtained at 304 and used to calculate the A/B ratio may be the B-mode image that underlies the elastography data in the elastography image obtained at 306 and explained in more detail below.

At 306, an elastography image is obtained. The elastography image may be a shear-wave elastography image or a strain elastography image. To acquire a shear-wave image, the ultrasound probe is controlled to enter the shear-wave mode. Once the probe is in the shear-wave mode, the probe is configured or controlled by the elastography circuit of the ultrasound imaging system (e.g., elastography circuit 103) to deliver a pushing pulse to generate a shear-wave within the ROI. After the shear-wave is generated, the probe measures the echoes scattered from the ROI as the shear-wave passes through the ROI. The processor of the ultrasound imaging system (e.g., processor 116) receives the electrical signals from the probe. The processor processes sets of vector data values, which correspond to shear-wave data from the electrical signals, where each set defines an individual shear-wave image frame. The shear-wave data vector values associated with the shear-wave image frame may be converted to Cartesian coordinates to generate shear-wave images formatted for display. To generate strain images, while the probe generates the mechanical (e.g., surface vibration, freehand or step quasi-static surface displacement, or the like) or radiation force on the patient or ROI, the probe measures the echoes scattered from the ROI before and after the ROI is compressed by the mechanical or radiation force. The processor receives the electrical signals from the probe and processes sets of vector data values corresponding to strain data from the electrical signals, where each set defines an individual strain image frame. The strain data vector values may be converted to Cartesian coordinates to generate the strain images formatted for display.

The elastography image obtained at 306 may include the ROI, as the elastography image may be obtained around the same time as the B-mode image (e.g., immediately after). The elastography image that is obtained at 306 may be acquired by the ultrasound system in response to the request to calculate the A/B ratio. In other examples, the elastography image may be obtained from memory. In some examples, the elastography image obtained at 306 may be selected by a user, e.g., the operator of the ultrasound imaging system may select an elastography image from a plurality of elastography images stored in memory of the ultrasound imaging system, or the operator may indicate via user input that a currently-displayed elastography image may be used for the A/B ratio calculation. The elastography image may include color or grayscale elastography information indicative of measured tissue stiffness, and the elastography information may be displayed as an overlay on a B-mode image. For example, the operator of the ultrasound imaging system may image the patient in B-mode and may identify the ROI in a B-mode image. The operator may then enter a user input requesting to image the patient in elastography mode, and the last B-mode image may be displayed with the elastography information overlaid on the B-mode image. Thus, the underlying B-mode image of the elastography image may be the B-mode image that is obtained at 304.

At 308, the elastography image may be processed. The processing of the elastography image may include adjusting the gain and/or transparency of the elastography image. For example, the gain of the elastography image may be adjusted to a maximum allowable gain and the transparency of the elastography image may be adjusted to a minimum transparency (e.g., a transparency of zero). In another example, the transparency may be set to a level based on a brightness of the underlying B-mode image, for example, increased transparency with decreasing brightness, such as a proportional linear relationship or based on a preset transfer function stored in the system and/or adjusted by the user. Such adjustments can advantageously allow some of the B-mode image information to be available to assist in improved segmentation by the A/B ratio model.

As explained above, the elastography data may be displayed over a B-mode image. When viewing an elastography image, a user may adjust the transparency and/or gain of the elastography information to enable the underlying B-mode image features to be visualized. However, the image segmentation of the elastography image that is performed to calculate the A/B ratio may be more robust and consistent across images if the transparency of the elastography information is set to the minimum transparency. Likewise, the robustness and consistency of the segmentation may be increased if the elastography information gain is increased to the maximum gain. The transparency and/or gain of the elastography image that is input to the A/B ratio model may be adjusted relative to and be different from a default transparency and/or gain. The default transparency and/or gain may be applied when an elastography image is first displayed, and a user may further adjust the transparency and/or gain based on user preferences. Thus, at least in some examples, the processing of the elastography image may result in a processed elastography image that has a different transparency and/or gain than the elastography image that was displayed to the user.

At 310, the B-mode image and the processed elastography image are entered as inputs to an A/B ratio model. The A/B ratio model (e.g., A/B ratio model 208) may include one or more a deep learning/machine learning models trained to identify the ROI/anatomical feature of interest in the B-mode image and in the elastography image. The A/B ratio model may perform image segmentation on the B-mode image and the elastography image to identify the borders of the ROI (e.g., the borders of the lesion in both the B-mode image and the elastography image) and then measure the width or area of the ROI in each image to calculate the A/B ratio. The segmentation of the ROI in the B-mode image may be performed independently of the segmentation of the ROI in the elastography image.

Thus, as indicated at 312, the A/B ratio model may segment the elastography image to identify and define the borders of the ROI and determine a width or an area (referred to as width or area A) of the ROI. As indicated at 314, the A/B ratio model may segment the B-mode image to identify and define the borders of the ROI and determine a width or an area (referred to as width or area B) of the ROI. The A/B ratio is then calculated by dividing the width or area of the ROI in the elastography image (A) by the width or area of the ROI in the B-mode image (B).

At 316, the A/B ratio may be stored in memory of the ultrasound imaging system and/or output for display on a display device (e.g., display device 118 or display device 234). Further, the A/B ratio may be sent to a remote device, such as a device storing an electronic medical record database and/or a picture archiving and communication system (e.g., as part of a patient exam that includes ultrasound images of the patient). Method 300 then returns.

Figure 4:
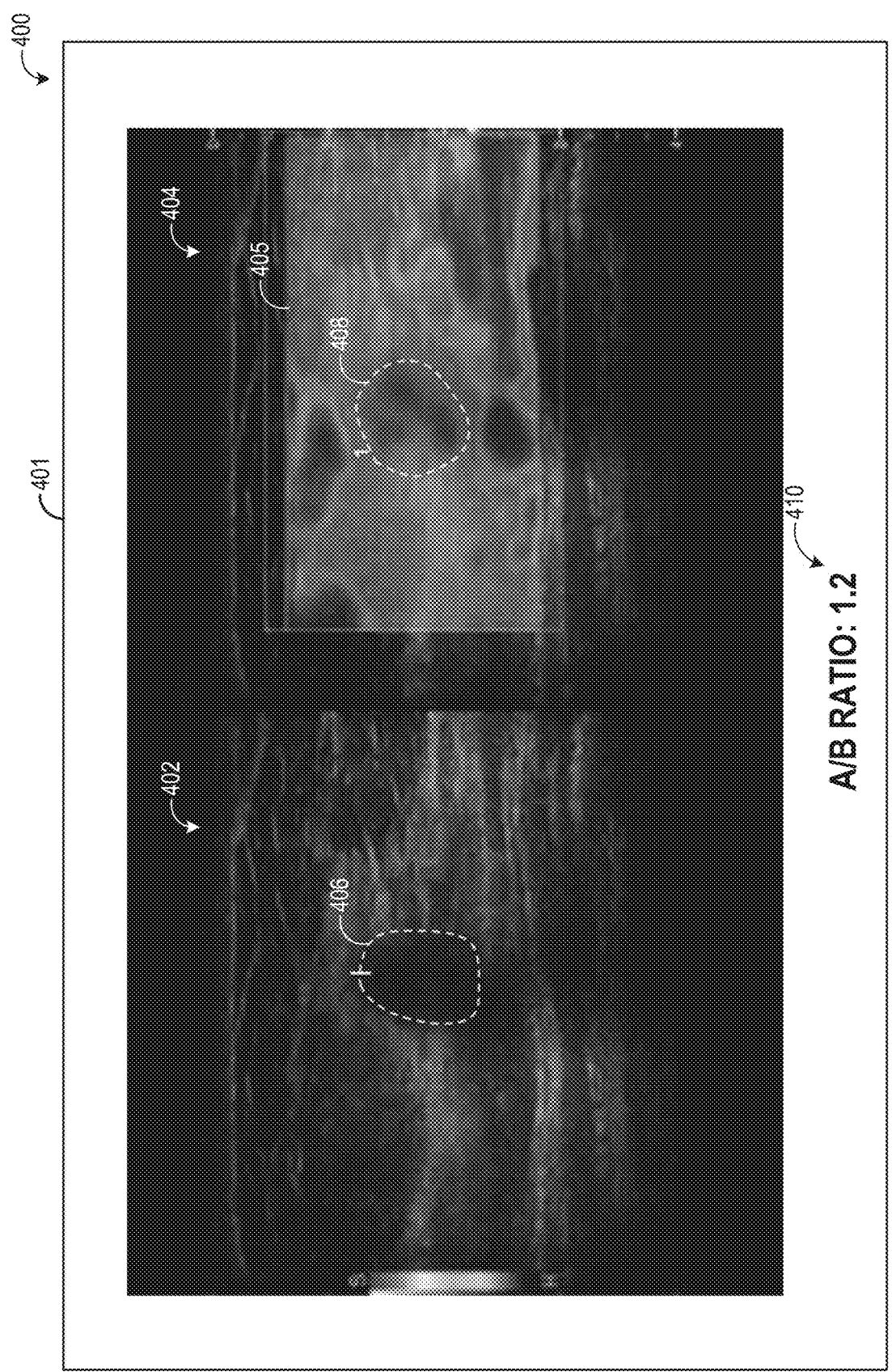
FIG. 4 shows an example graphical user interface showing an example B-mode image, an example elastography image, and an A/B ratio calculated according to the method of FIG. 3.

FIG. 4 shows an example graphical user interface (GUI) 400 that may be displayed on a display device 401 (such as display device 118 and/or display device 234). GUI 400 may include a B-mode image 402 and an elastography image 404. The elastography image 404 may include the B-mode image 402 and an overlay 405 of elastography information. The overlay 405 is shown in grayscale, with pixel brightness corresponding to an indicator of tissue stiffness (e.g., Young's modulus) as measured by the ultrasound probe in elastography mode. Alternatively, the overlay 405 may depict the elastography information in color.

The results from the A/B model image segmentation are also shown in GUI 400. For example, the border of a lesion as identified by the A/B model is depicted in dashed lines on both images. Thus, GUI 400 includes a border 406 of the lesion in the B-mode image 402 and a border 408 of the lesion in the elastography image 404. By displaying the images that were entered as input to the A/B model as well as the identified ROI borders, a user may be informed of the information used to calculate the A/B ratio. If the user disagrees with the identified borders (e.g., determines the borders are too small, too large, or that a lesion was incorrectly identified) or determines the image quality was insufficient to reliably identify the ROI borders, the user may reject the calculated A/B ratio, request a new A/B ratio be calculated, manually calculate an A/B ratio, etc. The A/B ratio calculated by the A/B ratio model is shown at 410. As explained above, the A/B ratio (herein, 1.2) is the ratio of the area/width of a ROI of an elastography image to an area/width of the ROI in a B-mode image. Thus, the A/B ratio shown at 410 is determined by dividing the width/area of border 408 by the width/area of border 406.

A technical effect of automatically determining an A/B ratio of a region of interest in an ultrasound image is reduced operator workflow and increased consistency of A/B ratio calculation across patients and imaging sessions.

An embodiment of a method includes automatically determining an A/B ratio of a region of interest (ROI) via an A/B ratio model that is trained to output the A/B ratio using a B-mode image of the ROI and an elastography image of the ROI as inputs, and displaying the A/B ratio on a display device. In a first example of the method, the A/B ratio is a ratio of a first area of the ROI in the elastography image to a second area of the ROI in the B-mode image, or the A/B ratio is a ratio of a first width of the ROI in the elastography image to a second width of the ROI in the B-mode image. The area of the ROI in each image may be determined by identifying the largest width/segment of the ROI and calculating the area from the largest width/segment. In other examples, the area of the ROI in each image may be determined by identifying the number of pixels in each ROI. When the A/B ratio is a ratio of widths, the widths may be the largest width/segment of each ROI. In a second example of the method, which optionally includes the first example, automatically determining the A/B ratio of the ROI via the A/B ratio model comprises: identifying a first border of the ROI in the elastography image via the A/B ratio model and determining the first area of the ROI in the elastography image based on the identified first border; identifying a second border of the ROI in the B-mode image via the A/B ratio model and determining the second area of the ROI in the B-mode image based on the identified second border; and determining the A/B ratio from the first area and the second area. In a third example of the method, which optionally includes one or both of the first and second examples, the elastography image is a shear-wave elastography image or a strain elastography image. In a fourth example of the method, which optionally includes one or more or each of the first through third examples, the elastography image includes the B-mode image and an overlay on the B-mode image, the overlay including elastography information indicating measured stiffness of tissue imaged in the B-mode image. In a fifth example of the method, which optionally includes one or more or each of the first through fourth examples, the method further includes, prior to entering the elastography image as input to the A/B ratio model, adjusting a transparency and/or a gain of the elastography image. In a sixth example of the method, which optionally includes one or more or each of the first through fifth examples, adjusting the transparency and/or the gain of the elastography image comprises adjusting the transparency to a minimum transparency and adjusting the gain to a maximum gain. In a seventh example of the method, which optionally includes one or more or each of the first through sixth examples, the method further comprises storing the A/B ratio in memory as part of a patient exam.

An embodiment for a system includes a display device; an ultrasound probe; a memory storing instructions; and a processor communicatively coupled to the memory and when executing the instructions, configured to: acquire, via the ultrasound probe, a B-mode image of a region of interest (ROI) of a patient; acquire, via the ultrasound probe, an elastography image of the ROI of the patient; enter the B-mode image and the elastography image as inputs to an A/B ratio model that is trained to output an A/B ratio of the ROI based on the B-mode image and the elastography image; and output the A/B ratio for display on the display device. In a first example of the system, the elastography image is acquired and/or processed to have a maximum gain and a minimum transparency. In a second example of the system, which optionally includes the first example, the transparency of the elastography image is a transparency of an overlay indicating measured stiffness of tissue of the patient, the overlay overlaid on the B-mode image. In a third example of the system, which optionally includes one or both of the first and second examples, the A/B ratio model includes a first image segmentation model trained to identify a first border of the ROI in the elastography image and a second image segmentation model trained to identify a second border of the ROI in the B-mode image. In a fourth example of the system, which optionally includes one or more or each of the first through third examples, the A/B ratio model determines a first area of the ROI in the elastography image based on the identified first border and determines a second area of the ROI in the B-mode image based on the identified second border, and determines the A/B ratio as a ratio of the first area to the second area. In a fifth example of the system, which optionally includes one or more or each of the first through fourth examples, the elastography image is a shear-wave elastography image or a strain elastography image.

An embodiment of a method for an ultrasound system includes receiving a request to determine an A/B ratio of a region of interest (ROI) of an elastography image, the elastography image including an underlying B-mode image and an overlay on the B-mode image, the overlay including elastography information of tissue imaged in the B-mode image and measured by an ultrasound probe of the ultrasound system; upon receiving the request, adjusting a transparency of the overlay of the elastography image to generate a processed elastography image; entering the processed elastography image and the underlying B-mode image as inputs to a model trained to output the A/B ratio based on the processed elastography image and the underlying B-mode image; and outputting the A/B ratio for display on a display device. In a first example of the method, receiving the request comprises receiving the request while the elastography image is displayed on the display device, the elastography image displayed with the overlay at a first transparency. In a second example of the method, which optionally includes the first example, adjusting the transparency comprises adjusting the transparency from the first transparency to a second transparency, the first transparency higher than the second transparency. In a third example of the method, which optionally includes one or both of the first and second examples, the A/B ratio is a ratio of a first area of the ROI in the elastography image to a second area of the ROI in the B-mode image. In a fourth example of the method, which optionally includes one or more or each of the first through third examples, the model is trained to identify and segment the ROI in the elastography image to determine the first area and identify and segment the ROI in the B-mode image to determine the second area. In a fifth example of the method, which optionally includes one or more or each of the first through fourth examples, receiving the request to determine the A/B ratio of the ROI comprises receiving a request to determine an A/B ratio of a lesion, the lesion imaged in the elastography image and the B-mode image.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method, comprising:
 receiving a request to determine an A/B ratio of a region of interest (ROI) of an elastography image displayed to a user on a display device, the elastography image including an underlying B-mode image displayed to the user on the display device and an elastography overlay displayed on the underlying B-mode image, the elastography overlay including elastography information of tissue imaged in the underlying B-mode image and measured by an ultrasound probe of an ultrasound system;
 in response to receiving the request, adjusting a gain of the elastography overlay of the elastography image to generate a processed elastography image that includes the underlying B-mode image and the adjusted-gain elastography overlay on the underlying B-mode image, the adjusted-gain elastography overlay having a different gain than the elastography overlay that is displayed to the user;
 entering the processed elastography image and a selected B-mode image of the ROI as inputs to an A/B ratio model that is trained to output the A/B ratio using the selected B-mode image of the ROI and the processed elastography image of the ROI as inputs, wherein the selected B-mode image is the underlying B-mode image or a different B-mode image that includes the ROI, and wherein the A/B ratio comprises a width and/or an area of the ROI in the elastography overlay relative to a width and/or an area of the ROI in the selected B-mode image; and
 displaying the A/B ratio on the display device.

2. The method of claim 1, wherein the elastography image is a shear-wave elastography image or a strain elastography image.

3. The method of claim 1, wherein the elastography overlay includes elastography information indicating measured stiffness of tissue imaged in the underlying B-mode image.

4. The method of claim 1, further comprising storing the A/B ratio in memory as part of a patient exam.

5. The method of claim 1, wherein the A/B ratio is a ratio of a first area of the ROI in the adjusted-gain elastography overlay to a second area of the ROI in the selected B-mode image.

6. The method of claim 5, wherein the A/B ratio of the ROI is determined via the A/B ratio model by:
identifying a first border of the ROI in the adjusted-gain elastography overlay via the A/B ratio model and determining the first area of the ROI in the adjusted-gain elastography overlay based on the identified first border;
identifying a second border of the ROI in the selected B-mode image via the A/B ratio model and determining the second area of the ROI in the selected B-mode image based on the identified second border; and
determining the A/B ratio from the first area and the second area.

7. The method of claim 1, wherein adjusting the gain of the elastography overlay of the elastography image to generate the processed elastography image further comprises adjusting a transparency and the gain of the elastography overlay to generate the processed elastography image.

8. The method of claim 7, wherein adjusting the transparency and the gain of the elastography overlay comprises adjusting the transparency to a minimum transparency and adjusting the gain to a maximum gain.

9. A system, comprising:
a display device;
an ultrasound probe;
a memory storing instructions; and
a processor communicatively coupled to the memory and when executing the instructions, configured to:
acquire, via the ultrasound probe, a B-mode image of a region of interest (ROI) of a patient;
acquire, via the ultrasound probe, an elastography image of the ROI of the patient, the elastography image including an elastography overlay on the B-mode image, the elastography overlay including elastography information of tissue imaged in the underlying B-mode image and measured by the ultrasound probe;
display the elastography image to a user on the display device;
receive a request to determine an A/B ratio of the ROI;
in response to the request, generate a processed elastography image that includes the B-mode image and an adjusted-gain elastography overlay on the B-mode image, wherein the adjusted-gain elastography overlay of the processed elastography image has a different gain than the elastography overlay of the elastography image that is displayed to the user;
enter the B-mode image and the processed elastography image as inputs to an A/B ratio model that is trained to output the A/B ratio of the ROI based on the B-mode image and the processed elastography image; and
output the A/B ratio for display on the display device, wherein the A/B ratio comprises a width and/or an area of the ROI in the elastography overlay relative to a width and/or an area of the ROI in the B-mode image.

10. The system of claim 9, wherein the elastography image is a shear-wave elastography image or a strain elastography image.

11. The system of claim 9, wherein the adjusted-gain elastography overlay is adjusted to have a maximum gain.

12. The system of claim 11, wherein the elastography overlay indicates measured stiffness of tissue of the patient.

13. The system of claim 9, wherein the A/B ratio model includes a first image segmentation model trained to identify a first border of the ROI in the processed elastography image and a second image segmentation model trained to identify a second border of the ROI in the B-mode image.

14. The system of claim 13, wherein the A/B ratio model determines a first area of the ROI in the processed elastography image based on the identified first border and determines a second area of the ROI in the B-mode image based on the identified second border, and determines the A/B ratio as a ratio of the first area to the second area.

15. A method for an ultrasound system, comprising:
displaying an elastography image to a user on a display device, the elastography image including an underlying B-mode image and an overlay on the B-mode image, the overlay including elastography information of tissue imaged in the B-mode image and measured by an ultrasound probe of the ultrasound system, the overlay displayed at a first transparency;
receiving a request to adjust a transparency of the overlay to a second transparency, and in response, adjusting the transparency of the overlay displayed on the display device to the second transparency;
receiving a request to determine an A/B ratio of a region of interest (ROI) of the elastography image displayed to the user on the display device, wherein the A/B ratio is a ratio of a first area of the ROI in the elastography image to a second area of the ROI in the B-mode image;
responsive to receiving the request, further adjusting the transparency of the overlay of the elastography image to a third transparency to generate a processed elastography image, wherein the processed elastography image includes the adjusted-transparency overlay with the third transparency on the underlying B-mode image, and wherein the third transparency is different than the first transparency;
entering the processed elastography image and the underlying B-mode image as inputs to a model trained to output the A/B ratio based on the processed elastography image and the underlying B-mode image; and
outputting the A/B ratio for display on a display device.

16. The method of claim 15, wherein the third transparency is a minimum transparency.

17. The method of claim 15, wherein third transparency is based on a brightness of the underlying B-mode image and the third transparency increases as the brightness decreases.

18. The method of claim 15, wherein the model is trained to identify and segment the ROI in the processed elastography image to determine the first area and identify and segment the ROI in the B-mode image to determine the second area.

19. The method of claim 15, wherein receiving the request to determine the A/B ratio of the ROI comprises receiving a request to determine an A/B ratio of a lesion, the lesion imaged in the elastography image and the B-mode image.

* * * * *